United States Patent
Iddawela et al.

(10) Patent No.: US 9,995,692 B2
(45) Date of Patent: Jun. 12, 2018

(54) SYSTEMS AND METHODS OF CONTROLLING A MANUFACTURING PROCESS FOR A MICROELECTRONIC COMPONENT

(71) Applicant: GLOBALFOUNDRIES, INC., Grand Cayman (KY)

(72) Inventors: Givantha Iddawela, Saratoga Springs, NY (US); Alok Vaid, Ballston Lake, NY (US)

(73) Assignee: GLOBALFOUNDRIES, INC., Grand Cayman (KY)

( * ) Notice: Subject to any disclaimer, the term of this patent is extended or adjusted under 35 U.S.C. 154(b) by 206 days.

(21) Appl. No.: 15/015,614

(22) Filed: Feb. 4, 2016

(65) Prior Publication Data

US 2016/0239012 A1  Aug. 18, 2016

Related U.S. Application Data

(60) Provisional application No. 62/117,577, filed on Feb. 18, 2015.

(51) Int. Cl.
| | |
|---|---|
| *G06F 19/00* | (2018.01) |
| *G01N 21/95* | (2006.01) |
| *G05B 19/418* | (2006.01) |
| *H01L 21/66* | (2006.01) |

(52) U.S. Cl.
CPC ... *G01N 21/9501* (2013.01); *G05B 19/41875* (2013.01); *G05B 2219/32179* (2013.01); *G05B 2219/32182* (2013.01); *G05B 2219/32187* (2013.01); *G05B 2219/45031* (2013.01); *H01L 22/10* (2013.01); *Y02P 90/22* (2015.11)

(58) Field of Classification Search
CPC .............. H01L 22/10; G05B 19/41875; G01N 21/9501
See application file for complete search history.

(56) References Cited

U.S. PATENT DOCUMENTS

| | | | | |
|---|---|---|---|---|
| 5,526,293 | A * | 6/1996 | Mozumder | G05B 13/042 700/109 |
| 6,925,347 | B1 * | 8/2005 | Miller | G05B 19/41875 438/14 |
| 2007/0238201 | A1 * | 10/2007 | Funk | H01L 22/12 438/14 |
| 2010/0135571 | A1 * | 6/2010 | Littau | G01B 11/0616 382/152 |

(Continued)

*Primary Examiner* — Vincent Tran
(74) *Attorney, Agent, or Firm* — Lorenz & Kopf, LLP

(57) ABSTRACT

Systems and methods for controlling manufacturing processes for microelectronic components are provided. In an exemplary embodiment, a method includes determining a specification range for a desired parameter. The microelectronic component is processed in a manufacturing tool, and a trace data set is recorded during the processing. An estimated trace data parameter is determined with the trace data set, and a first measured value of the microelectronic component is measured in a measurement tool. An estimated desired parameter is determined using the first measured value and the estimated trace data parameter, and the manufacturing process is adjusted when the estimated desired parameter is outside of the specification range.

20 Claims, 2 Drawing Sheets

(56) References Cited

U.S. PATENT DOCUMENTS

| | | | |
|---|---|---|---|
| 2013/0006406 A1* | 1/2013 | Aharoni | G05B 23/0216 |
| | | | 700/97 |
| 2015/0008132 A1* | 1/2015 | Stahl | C23C 18/1675 |
| | | | 205/83 |
| 2015/0012255 A1* | 1/2015 | Li | H01L 22/20 |
| | | | 703/6 |

* cited by examiner

SYSTEMS AND METHODS OF CONTROLLING A MANUFACTURING PROCESS FOR A MICROELECTRONIC COMPONENT

CROSS-REFERENCE TO RELATED APPLICATIONS

This application claims the benefit of U.S. Provisional Application No. 62/117,577, filed Feb. 18, 2015.

TECHNICAL FIELD

The technical field generally relates to systems and methods of controlling manufacturing processes for microelectronic components, and more particularly relates to measurement systems and methods for controlling manufacturing processes for microelectronic components.

BACKGROUND

The semiconductor industry is continuously moving toward the fabrication of smaller and more complex microelectronic components with higher performance. As a result, many microelectronic components in integrated circuits are becoming smaller and more complex. As the microelectronic components become smaller, the dimensions and/or composition of different features become smaller and have a greater impact on the proper operation of the integrated circuit. These small features should be measured from time to time for various reasons, such as to monitor the fabrication process, to guard against microscopic faults, to understand manufacturing steps or performance levels, etc. However, many microelectronic components of an integrated circuit have several different features. For example, a field effect transistor (FET) includes a source, a drain, a gate, and a gate dielectric. Each feature may vary somewhat in dimension or material property, and a change in any one of these features could impact the electrical performance of the microelectronic component.

Metrology is the science of measurement. One technique used in metrology is scatterometry. In scatterometry techniques, an object is illuminated with electromagnetic radiation, such as light, the light is scattered by the object, and the scattered light is measured at a variety of locations. A model is developed that predicts the intensity and phase change of the scattered light based on various dimensions and properties of the structure, such as the height, width, angle, reflectivity of the material, and composition of the object. The various dimensions and properties of the structure are referred to herein as "parameters." Various dimensions of the object can then be determined by comparing the actual measured scattered light to the model. However, many different parameters will scatter light, and each variable parameter of the object is represented as an unknown variable in the model. Having more unknown variables in the model increases the complexity of the comparison and reduces the accuracy of the measurement. For example, if the critical dimension is the depth of a valley between two towers, it is difficult to produce an accurate model when other parameters can vary in an unknown manner, such as variations in the distance between the two towers, the shape of the two towers, the composition of the two towers, intersection angles, etc. Measurement accuracy can be improved by using two or more different measurement tools where one or more of the parameters, such as the distance between the towers in the above example, is measured on a different metrology tool and fed forward into the scatterometry model. The scatterometry model will then fix the parameter at the value that was fed in, thereby reducing the number of unknown variables in the model and increasing accuracy. However, each additional measurement step increases the cycle time and manufacturing costs.

Accordingly, it is desirable to provide methods for measuring parameters that utilize a limited number of measurement tools, such as one measurement tool. In addition, it is desirable to provide methods for measuring parameters that utilize existing data without requiring additional measurement steps. Furthermore, other desirable features and characteristics of the various embodiments will become apparent from the subsequent detailed description and the appended claim, taken in conjunction with the accompanying drawings and this background.

BRIEF SUMMARY

Systems and methods for controlling manufacturing processes for microelectronic components are provided. In an exemplary embodiment, a method includes determining a specification range for a desired parameter. The microelectronic component is processed in a manufacturing tool, and a trace data set is recorded during the processing. An estimated trace data parameter is determined with the trace data set, and a first measured value of the microelectronic component is measured in a measurement tool. An estimated desired parameter is determined using the first measured value and the estimated trace data parameter, and the manufacturing process is adjusted when the estimated desired parameter is outside of the specification range.

A method for controlling a manufacturing process for a microelectronic component is provided in another embodiment. The method includes determining a specification range for a desired parameter of the microelectronic component, and processing the microelectronic component in a manufacturing tool. Sensor data is recorded during processing, and an estimated sensor data parameter is determined with the sensor data. A first measured value of the microelectronic component in measured in a single measurement tool, and an estimated desired parameter is determined using the first measured value and the estimated sensor data parameter. The manufacturing process is adjusted when the estimated desired parameter is outside of the specification range.

A system for controlling a manufacturing process for a microelectronic component is provided in yet another embodiment. The system includes a manufacturing tool with a manufacturing tool sensor, where the manufacturing tool is configured to process the microelectronic component and the manufacturing tool sensor is configured to produce a trace data set during processing. A measurement tool is configured to receive the microelectronic component after processing in the manufacturing tool, and to measure a first measured value of the microelectronic component. A computer is configured to receive the trace data set from the manufacturing tool and the first measured value from the measurement tool. The computer is also configured to produce an estimated trace data parameter with the trace data set and to determine an estimated desired parameter with a model that uses the estimated trace data parameter and the first measured value. The computer is further configured to adjust the manufacturing process when the estimated desired parameter is outside of a specification range.

BRIEF DESCRIPTION OF THE DRAWINGS

The present embodiments will hereinafter be described in conjunction with the following drawing figures, wherein like numerals denote like elements, and wherein.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

According to various embodiments described herein, parameters of a microelectronic component are measured using a model that correlates the response from a measurement tool to the parameters of the model. The parameters can be dimensions, compositions, densities, crystalline structure, etc. In an exemplary embodiment, the microelectronic component is a component in an integrated circuit and the measurement tool is a scatterometer, but other microelectronic components can be measured and other measurement tools can be used. Different parameters of the microelectronic component can influence the values from the measurement tool. The microelectronic component described herein, as an example, is a pair of towers, where the towers could be adjacent fins used to produce a finned field effect transistor (FinFET). However, many other structure or uses of the microelectronic component are also possible in other embodiments. The exemplary microelectronic component described herein (the two towers) includes many different parameters, where the parameters are features of the microelectronic component. In the exemplary embodiment where the microelectronic component is two towers, different parameters of the microelectronic component include the depth of the valley between the towers, the shape of the towers, the distance between the towers, the composition of the towers, etc. As an example, the pattern of scattered light in the scatterometer may depend on many different parameters, including but not limited to (1) the depth of a valley between two towers, (2) the shape of the towers, (3) the distance between the towers, and (4) the composition of the towers. Depending on the complexity of the microelectronic component, it may be difficult to prepare a model that accounts for every possible variation in the microelectronic component. The establishment of accurate values for one or more parameters greatly increases the measurement accuracy of the model and the measurement tool for the desired parameter. A model can be produced that utilizes the sensor data to generate a reliable estimate of one or more parameters, and this reliable estimate can then be used to increase the measurement accuracy of the model and the measurement tool for determining a different, desired parameter.

Figure 1:
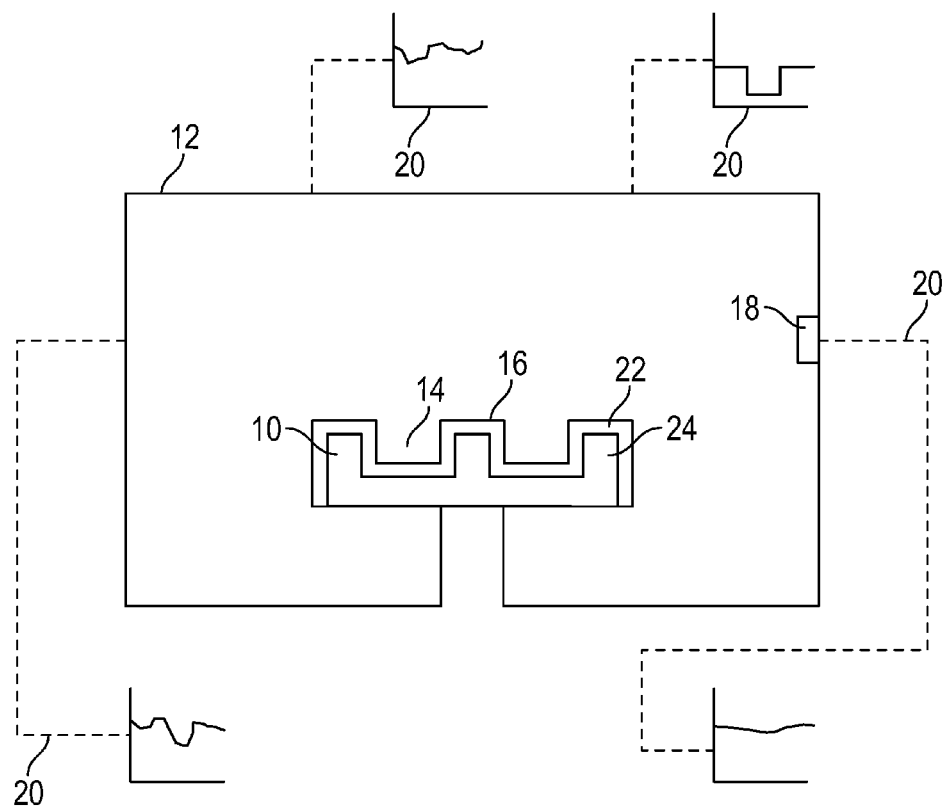
FIG. 1 is a schematic drawing of a manufacturing tool with a microelectronic component.

In an exemplary embodiment illustrated in FIG. 1, a microelectronic component 10 is processed in a manufacturing tool 12, wherein the processing is at least one part of a manufacturing process for the microelectronic component 10. The manufacturing process may include a plurality of processing steps using a plurality of manufacturing tools 12. An exemplary embodiment is described in this description for illustration purposes, where the microelectronic component 10 in the exemplary embodiment is a microelectronic device with a valley 14 and adjacent towers 16. A "microelectronic device," as used herein, means a plurality of interconnected electronic components positioned on a substrate, such as a crystalline silicon substrate. However, it should be understood that alternate embodiments many include many different microelectronic components 10 with different structures, and the microelectronic component 10 may or may not have a tower 16 and/or a valley 14 in every embodiment. The microelectronic component 10 includes several parameters, where the parameters are dimensions, shapes, compositions, etc. As an example, a masking layer 22 is formed overlying a support 24, wherein the towers 16 of the microelectronic component 10 include the masking layer 22 and the support 24. As used herein, the term "overlying" means "over" such that an intervening layer may lie between the masking layer 22 and the support 24, or "on" such that the masking layer 22 physically contacts the support 24. In this exemplary embodiment, the desired parameter is the depth of the valley 14 between the towers 16.

In an exemplary embodiment, the manufacturing tool 12 is an epitaxial growth station where the masking layer 22 is epitaxially grown overlying the supports 24, and the masking layer 22 may also overlie other portions of the microelectronic component 10. The manufacturing tool 12 may be any of the tools used in the manufacture of microelectronic devices 10, including but not limited to the epitaxial growth station, a reactive ion etch tool, a wet etch tool, a chemical vapor deposition tool, an atomic vapor deposition tool, and a chemical mechanical planarization tool. The composition of the masking layer 22 depends on the conditions in the epitaxial growth station, such as the temperature, pressure, and the flow rates and compositions of the gases present. The various conditions are measured by one or more manufacturing tool sensors 18, where the measurements are continuously recorded as a trace data set 20. As used herein, a "trace data set" means a measured property in the manufacturing tool 12 that is continuously measured and recorded. The trace data set 20 may be recorded in a chart where the horizontal "X" axis is time, and the vertical "Y" axis is the value of the condition being measured. In many cases, the trace data set 20 may be correlated to a specific parameter of the microelectronic component 10, referred to herein as a trace data parameter. For example, manufacturing conditions such as the composition of the gases, temperatures, pressures, flow rates, etc., may be correlated to the composition of the masking layer 22. Therefore, the trace data set 20 for those conditions in the manufacturing tool 12 can be correlated with the trace data parameter (e.g., the composition of the masking layer 22) to develop an estimated trace data parameter. In an alternate embodiment, non-continuous sensor data may be used in place of the trace data set 20 or in conjunction with the trace data set 20 to develop an estimated sensor data parameter that is similar to the estimated trace data parameter. "Sensor data," as used herein, means data collected by a manufacturing tool sensor 18 within a manufacturing tool 12 during manufacture of a microelectronic component 10. A trace data set 20 is continuous sensor data, but not all sensor data is continuous so some sensor data may not be a trace data set 20. The estimated sensor data parameter may be used in place of the estimated trace data parameter described below in some embodiments.

Many manufacturing tool sensors 18 collect information, but the collected information may not be perfectly accurate in all cases. For example, an actual temperature of 25.00 degrees Celsius (° C.) may produce a thermometer reading of 25.1° C. As such, the estimated trace data parameter is an approximation of the actual trace data parameter. For example, the estimated trace data parameter may be accurate to within about 1 percent or less of the actual trace data parameter, or about 3 percent or less or about 5 percent or less in alternate embodiments. The trace data set 20 that is correlated with the trace data parameter may be one or more trace data sets 20. In some cases, a combination of different trace data sets 20 and/or sensor data provide a more accurate estimated trace data parameter than a single trace data set 20, and there may be one or more estimated trace data parameters in various embodiments.

Figure 2:
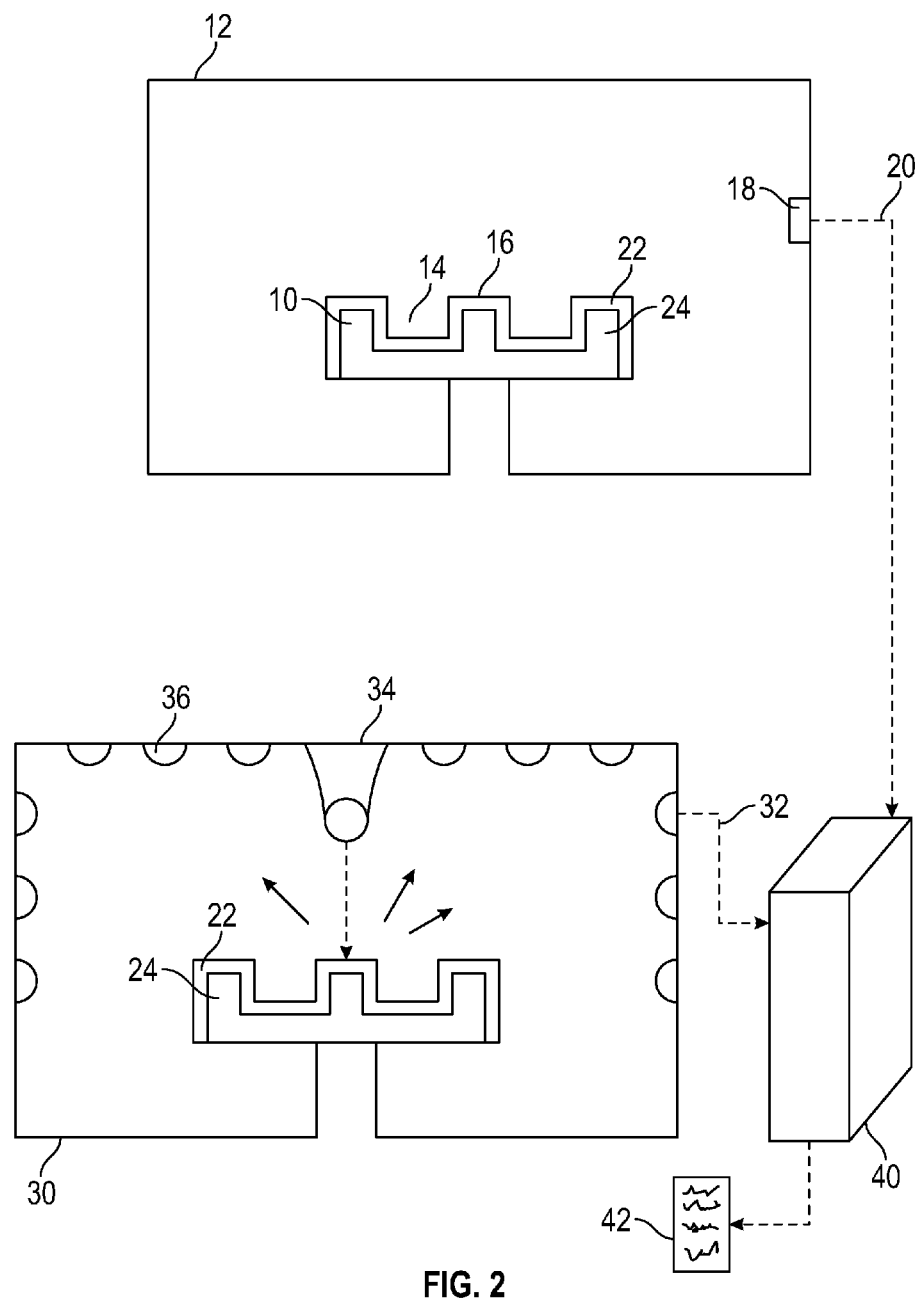
FIG. 2 is a schematic drawing of tools and a method for measuring a parameter of the microelectronic component.

Reference is made to FIG. 2. The microelectronic component 10 is transferred from the manufacturing tool 12 to a measurement tool 30, where the manufacturing tool 12 is illustrated to show the source of the trace data set 20. The measurement tool 30 provides a first measured value 32 for the microelectronic component 10. In an exemplary embodiment, the measurement tool 30 is a scatterometer including a light source 34 and a plurality of measurement tool sensors 36, but other measurement tools 30 can be used in other embodiments, such as a scanning electron microscope. The plurality of measurement tool sensors 36 are positioned about the scatterometer to measure the scattered light at various locations. In the scatterometer, the light source 34 is directed at the microelectronic component 10, and may produce a light spot about 40 microns in diameter. The light source 34 may be a broad band source, but narrow band light sources 34 or other electromagnetic sources may be used in other embodiments. Some of the light is scattered upon contact with the microelectronic component 10, and the scattered light is measured with the plurality of measurement tool sensors 36. Many different parameters of the microelectronic component 10 influence how the light is scattered. In an exemplary embodiment, at least the desired parameter and the trace data parameter influence the first measured value 32 from the measurement tool 30. In the example described herein, at least the composition of the masking layer 22 (the trace data parameter) and the valley depth (the desired parameter) both influence how the light is scattered from the microelectronic component 10 in the scatterometer. Other parameters may also influence the first measured value 32 from the measurement tool 30, where different parameters may have different influences in different types of measurement tools 30.

A model is developed to correlate the first measured value 32 with the desired parameter. The model may account for optical properties of the microelectronic component 10, dimensions of the microelectronic component 10, etc., where the optical properties may depend on the composition of various parts of the microelectronic component 10 (such as the composition of the masking layer 22.) When many different parameters influence a measurement tool 30, it becomes difficult to accurately model a limited number of parameters because some variations in different parameters can produce similar effects. In general, most models are simpler when there are fewer variables, and each parameter that can vary is generally included in the model as a variable. In an exemplary embodiment, the model is a semi-analytical mathematical model.

The model may be stored and run on a computer 40 in some embodiments. The estimated trace data parameter may be determined from the trace data set 20 as a part of the model, or the estimated trace data parameter may be determined from the trace data set 20 prior to entry into the model. In either embodiment, the estimated trace data parameter is determined from the trace data set 20 provided by the manufacturing tool 30. The estimated trace data parameter is used as a known value in the model, and thereby effectively reduces the number of variables in the model. The reduced number of variables increases the accuracy of the model in determining an estimated desired parameter 42 based on the first measured value 32 and the estimated trace data parameter. The estimated desired parameter 42 is an approximation of the actual desired parameter. For example, the estimated desired parameter 42 may be accurate to within about 1 percent or less of the actual desired parameter, or about 3 percent or less or about 5 percent or less in various embodiments.

In an exemplary embodiment, the manufacturing process may be adjusted based on the determination of the estimated desired parameter 42. In an exemplary embodiment, a specification range is determined for a desired parameter of the microelectronic component 10, where the specification range is intended to produce quality microelectronic components 10. The manufacturing process may be adjusted if the estimated desired parameter 42 is outside of a set range, where the set range may be the specification range for the actual desired parameter. In an alternate embodiment, the set range may be a process adjustment range for the actual desired parameter, where the process adjustment range may be intended to keep other parameters within desired ranges, or the process adjustment range may be intended to keep the desired parameter within a range more narrow than the specification range. The adjustment of the manufacturing process may involve an adjustment of a process condition for the manufacturing tool 12 that produced the trace data set 20, but in alternate embodiments one or more process conditions in a different manufacturing tool may be adjusted. For example, the valley 14 between the towers 16 in the example described herein may be formed in a reactive ion etch tool, and the masking layer 22 may be formed in an epitaxial growth station, where the trace data set 20 is measured and recorded in the epitaxial growth station. The manufacturing process may be adjusted in one or more of either the reactive ion etch tool, the epitaxial growth station, or other manufacturing tools in various embodiments.

A system may be used in some embodiments, where the system includes the manufacturing tool 12 with the manufacturing tool sensor 18. The manufacturing tool 12 may be configured to process the microelectronic component and the manufacturing tool sensor 18 is configured to produce the trace data set 20 as described above. The system also includes the measurement tool 30 that is configured to receive the microelectronic component 10 after processing in the manufacturing tool 12, and the measurement tool 30 is configured to measure the first measured value 32, as described above. The system includes the computer 40 that is configured to receive the trace data set 20 and the first measured value 32 and produce the estimated desired parameter 42 using the model, the estimated trace data parameter, and the first measured value 32, again as described above. The collection of items in the system can be used to adjust the manufacturing process or to take other actions, all as described above.

In accordance with embodiments described herein, an accurate estimated desired parameter 42 can be produced by using a single measurement tool 30 combined with trace data set 20 from a manufacturing tool 12. The accuracy of the estimated desired parameter 42 using the trace data set 20 and the estimated trace data parameter is generally greater than the accuracy of an estimated desired parameter 42 produced by a single measurement tool 30 that does not use a trace data set 20 and does not use measurement data from another measurement device or tool. However, the use of the trace data set 20 does not increase the number of transfer steps for the microelectronic component 10. The use of a single measurement tool 30 may shorten and simplify the manufacturing process compared to the use of more than one measurement tool 30, because there is no transfer of the microelectronic component 10 from one measurement tool 30 to the next. The following hypothetical example may further clarify the description above.

Hypothetical Example

A 20 nanometer (nm) tri-layer masking layer 22 is produced using epitaxy in an epitaxial growth station. The resulting microelectronic component 10 has the tri-layer masking layer 22 with 3 layers, where the 3 layers are an L1 layer, an L2 layer, and an L3 layer (not individually illustrated). Each of the 3 layers has a germanium percentage and a thickness, and the accurate measurement of the germanium percentage and thickness of each layer is not possible in a single metrology technique. The temperature, pressure, gas flow rates, and gas compositions are continuously measured as a trace data set 20 during the processing of the tri-layer masking layer 22 in the epitaxial growth station (the manufacturing tool 12). The trace data set 20 is used to produce an estimated germanium concentration and an estimated thickness for each of the L1 layer, the L2 layer, and the L3 layer, where the estimated germanium concentration and the estimated thickness are exemplary estimated trace data parameters. The microelectronic component 10 is then moved from the epitaxial growth station to a scatterometer, and a first measured value 32 (and perhaps other measured values) are produced in the scatterometer. A model is then used to develop an estimated total tri-layer masking layer thickness, where the model uses the measured values from the scatterometer. The estimated total tri-layer masking layer thickness can then be compared to the sum of the individual estimated thicknesses for the L1 layer, the L2 layer and the L3 layer. The initial estimated thicknesses for the L1 layer, the L2 layer, and the L3 layer based on the trace data set 20 can then be adjusted within the model such that the sum of the three thicknesses matches the estimated total tri-layer masking layer thickness developed by the scatterometer. The compositions of the individual layers influence the optical properties of the tri-layer masking layer 22, so the model uses the estimated germanium concentration to more accurately estimate the total tri-layer masking layer thickness. The adjusted estimates for the thicknesses of the three layers and for the total thickness of the tri-layer masking layer 22 may then be used to determine performance criteria, for quality control, for adjustments to further manufacturing processes, or as otherwise useful for the manufacturer.

While at least one exemplary embodiment has been presented in the foregoing detailed description, it should be appreciated that a vast number of variations exist. It should also be appreciated that the exemplary embodiments are only examples, and are not intended to limit the scope, applicability, or configuration of the application in any way. Rather, the foregoing detailed description will provide those skilled in the art with a convenient road map for implementing one or more embodiments, it being understood that various changes may be made in the function and arrangement of elements described in an exemplary embodiment without departing from the scope, as set forth in the appended claims.

What is claimed is:

1. A method of controlling a manufacturing process for a microelectronic component comprising:
    determining a specification range for a desired parameter of the microelectronic component;
    processing the microelectronic component in a manufacturing tool;
    recording a trace data set while processing the microelectronic component in the manufacturing tool;
    determining an estimated trace data parameter with the trace data set, wherein the estimated trace data parameter is a dimension or property of the microelectronic component;
    measuring a first measured value of the microelectronic component in a measurement tool;
    determining an estimated desired parameter using the first measured value and the estimated trace data parameter, wherein the estimated desired parameter is a dimension or property of the microelectronic component that is different than the estimated trace data parameter; and
    adjusting the manufacturing process when the estimated desired parameter is outside of the specification range for the desired parameter.

2. The method of claim 1 wherein measuring the first measured value comprises measuring the first measured value in a scatterometer.

3. The method of claim 1 wherein measuring the first measured value comprises measuring the microelectronic component with one measurement tool.

4. The method of claim 1 further comprising:
    adjusting the manufacturing process when the estimated desired parameter is within the specification range but outside of a process adjustment range.

5. The method of claim 1 wherein the estimated trace data parameter is determined prior to measuring the first measured value.

6. The method of claim 1 wherein determining the estimated trace data parameter of the microelectronic component comprises using a plurality of trace data sets.

7. The method of claim 1 further comprising:
    developing a model to determine the estimated desired parameter using the first measured value and at least one estimated trace data parameter.

8. A method of controlling a manufacturing process for a microelectronic component comprising:
    determining a specification range for a desired parameter of the microelectronic component;
    processing the microelectronic component in a manufacturing tool;
    recording a sensor data while processing the microelectronic component in the manufacturing tool;
    determining an estimated sensor data parameter with the sensor data, wherein the estimated sensor data parameter is a dimension or property of the microelectronic component;
    measuring a first measured value of the microelectronic component in a single measurement tool;
    determining an estimated desired parameter using the first measured value and the estimated sensor data parameter, wherein the estimated desired parameter is a dimension or property of the microelectronic component that is different than the estimated sensor data parameter; and
    adjusting the manufacturing process when the estimated desired parameter is outside of the specification range.

9. The method of claim 8 wherein the estimated sensor data parameter is determined prior to measuring the first measured value of the microelectronic component.

10. The method of claim 8 wherein determining the estimated sensor data parameter comprises determining the estimated sensor data parameter with a plurality of sensor data.

11. The method of claim 8 wherein determining the estimated desired parameter comprises using a model to determine the estimated desired parameter.

12. The method of claim 8 wherein determining the estimated sensor data parameter comprises correlating the estimated sensor data parameter with the sensor data.

13. The method of claim 8 further comprising:
developing a model to determine the estimated desired parameter from the first measured value and the estimated sensor data parameter.

14. A system for controlling a manufacturing process for a microelectronic component comprising:
a manufacturing tool comprising a manufacturing tool sensor, wherein the manufacturing tool is configured to process the microelectronic component, and wherein the manufacturing tool sensor is configured to produce a trace data set during processing within the manufacturing tool;
a measurement tool configured to receive the microelectronic component after processing in the manufacturing tool, and wherein the measurement tool is further configured to measure a first measured value of the microelectronic component; and
a computer configured to receive the trace data set from the manufacturing tool and the first measured value from the measurement tool, wherein the computer is configured to produce an estimated trace data parameter of the microelectronic component with the trace data set, and wherein the computer is configured to determine an estimated desired parameter with a model, wherein the estimated trace data parameter and the estimated desired parameter are different dimension (s) or property(ies) of the microelectronic component, wherein the model is configured to use the estimated trace data parameter and the first measured value to determine the estimated desired parameter, and wherein the computer is configured to adjust the manufacturing process when the estimated desired parameter is outside of a specification range.

15. The system of claim 14 wherein the measurement tool comprises a scatterometer.

16. The system of claim 14 wherein the measurement tool comprises one measurement tool.

17. The system of claim 14 wherein the computer is further configured to adjust the manufacturing tool when the estimated desired parameter is outside of the specification range.

18. The system of claim 14 wherein the computer is configured to utilize a correlation between the estimated trace data parameter and the trace data set to determine the estimated trace data parameter.

19. The system of claim 14 wherein the computer is configured to utilize a correlation between the estimated trace data parameter and a plurality of trace data sets to determine the estimated trace data parameter.

20. The system of claim 14 wherein the manufacturing tool is selected from the group consisting of an epitaxial growth tool, a reactive ion etch tool, a wet etch tool, a chemical vapor deposition tool, an atomic vapor deposition tool, and a chemical mechanical planarization tool.

* * * * *